United States Patent [19]
Winberg et al.

[11] 4,246,906
[45] Jan. 27, 1981

[54] APPARATUS FOR SELF-MONITORING OF PHYSIOLOGICAL VARIABLES

[76] Inventors: Jack S. Winberg, 619 Central, Wilmette, Ill. 60091; Richard A. Karlin, 3732 N. Lawndale, Chicago, Ill. 60618

[21] Appl. No.: 53,502

[22] Filed: Jun. 28, 1979

Related U.S. Application Data

[63] Continuation of Ser. No. 837,372, Sep. 28, 1977, abandoned.

[51] Int. Cl.³ ............................................. A61B 5/00
[52] U.S. Cl. ................................... 128/736; 128/905
[58] Field of Search ............... 128/731, 732, 736, 903, 128/904, 905, 701

[56] References Cited
U.S. PATENT DOCUMENTS

| | | | |
|---|---|---|---|
| 3,769,965 | 11/1973 | Raddi et al. | 128/701 |
| 3,871,362 | 3/1975 | Dunegan | 128/736 |
| 3,924,606 | 12/1975 | Silva et al. | 128/732 |
| 3,942,516 | 3/1976 | Glynn et al. | 128/732 |
| 4,170,225 | 10/1979 | Criglar et al. | 128/732 |

*Primary Examiner*—William E. Kamm
*Attorney, Agent, or Firm*—Irwin C. Alter; Phillip A. Weiss

[57] ABSTRACT

A supporting surface establishes a positional relationship between a sensor and an anatomical site which is to be monitored. The supporting surface may also act as an enclosure and as an acoustic baffle. An electronic circuit produces visible and audible output responsive to changes in a property of the sensor and therefore to changes in the physiological variable being monitored. The output may be used for physiological monitoring or for biofeedback training. The output format, the control placement, and the supporting surface make possible an improved biofeedback training method.

10 Claims, 3 Drawing Figures

APPARATUS FOR SELF-MONITORING OF PHYSIOLOGICAL VARIABLES

This is a continuation of application Ser. No. 837,372, filed Sept. 28, 1977, now abandoned.

BACKGROUND AND SUMMARY OF THE INVENTION

This invention relates to apparatus for monitoring physiological variables, and more particularly relates to apparatus for producing audible and visible output responsive to changes in a physiological variable such as the temperature of a human fingertip.

Monitoring of physiolgical variables is important to researchers, doctors, physiologists, and persons who wish to learn to exercise control over processes which are mediated autonomically, hormonally, or reflexly. Such monitoring is indispensable to persons who wish to achieve muscular relaxation, said relaxation being inversely proportional to the activity of the sympathetic branch of the autonomic nervous system.

For example, the temperature of an extremity, such as a fingertip, is proportional to the rate of blood flow through the extremity. The autonomic nervous system controls the rate of blood flow (circulation) to all parts of the body including the extremities. Sympathetic stimulation reduces the blood flow to the extremities. Thus, fingertip temperature varies inversely with the activity of the sympathetic branch of the autonomic nervous system, and monitoring fingertip temperature and rendering it in visible or audible form reveals the state of activity of the sympathetic nervous system, as well as the related state of skeleto-muscular and smooth muscular relaxation.

Such relaxation reduces stress created ailments such as high blood pressure, tension, and headaches.

Existing devices for monitoring physiological variables have serious deficiencies. One such deficiency is the use of electrodes. These conductive elements are used to establish conductive electrical contact with the anatomical site being monitored. In contrast to electrodes, there exist 'sensors' which do not require conductive electrical contact with the anatomical site being monitored.

The contact resistance between such an electrode and the anatomical site depends on the surface state of the electrode, the surface state of the anatomical site, the shapes of the electrode and the site, the pressure between electrode and site, and divers other factors. Sometimes conductive creams must be used to improve contact. The contact resistance is extremely variable and almost impossible to control or reproduce. Thus, even experienced professionals suffer great difficulties when using electrodes.

Another such deficiency is the use of either electrodes or sensors which are attached to the main apparatus by means of electrical cables. The cables are subject to tangling and breakage. The cable connectors frequently develop contact problems. The electrodes or sensors must be taped or fastened to the body. Further, while non-electrically contacting sensors do not depend on electrically conductive contact with the body, they do depend on reasonably consistent physical contact and this is hard to achieve through taping or tying. Also, the relatively unprotected sensors are easily damaged.

Yet other deficiencies include complex controls requiring operator training, complex output formats requiring professional interpretation, excessive power consumption and large size thus limiting portability and location of use, and high cost tending to limit ownership to a small group of professionals.

One attempt to overcome a few of these deficiencies is described in U.S. Pat. No. 3,648,686 (Payne—Mar. 14, 1972). Unfortunately, the Payne device still has a number of serious disadvantages. Firstly, it utilizes electrodes to sense galvanic ski response and therefore it is subject to all of the attendant ills of electrodes. Secondly, it lacks visual output. Thirdly, its audible output is a continuous tone, an output format which has been found to be fatiguing to the listener. Fourthly, galvanic skin response does not correlate as well with muscular relaxation as do other methods such as peripheral circulation thermography.

It has been discovered that all of these aforementioned deficiencies can be overcome by a radical approach which places a sensor, said sensor not depending on conductive electrical contact with the anatomical site being monitored, in the wall of a supporting surface wherein the shape of the supporting surface and the positional relationship of the sensor to the surface serve to establish the required positional relationship between the sensor and the anatomical site being monitored, and which combines these with an audible transducer, a visible transducer, a control, a novel electronic circuit, and a battery such that variation of a physiological variable of the anatomical site adjacent to the sensor and support surface causes variation of output from at least one of the transducers.

The electronic circuit includes a novel tone circuit and an interupter circuit. Power consumption is minimized through the use of complimentary-metal-oxide-semiconductor integrated circuits (CMOS) and through a unique series output circuit. A loud speaker and a light emitting diode supply audible and visible output. The control connects to the tone circuit and establishes an initial operating tone. An On-Off switch is linked to the control. Power is supplied by a nine volt battery, assuring safe operation.

The CMOS circuits are members of a family of circuits designated 74C and intended primarily for digital use. The present invention uses them for both digital and analog functions thus realizing very low power consumption and low cost.

Traditionally, a tone is made to vary in accordance with the parametric variations of a sensor by utilizing the snesor as one of the frequency determining components of an oscillator circuit. This method suffers from limited sensitivity. Greater sensitivity can be obtained through the use of a bridge followed by amplification. However, a bridge requires three additional stable components and an amplifier adds power consumption and cost.

It has been discovered that great sensitivity at low cost and low power consumption can be obtained through a novel configuration of an integrator and a Schmitt type trigger. This configuration is especially favorable in conjunction with CMOS circuitry. Further, such a configuration provides easy initial adjustability and can be arranged to provide for comparison monitoring between two like sensors.

It has further been discovered that a pleasing and effective output format can be realized by using an interupter to periodically start and stop an output tone and by combining a loudspeaker of falling low frequency amplitude with a filter capacitor and an acoustic baffle.

It is one object of the present invention to provide a monitor of physiological variables which utilizes an electrically non-contacting sensor rather than electrodes.

Another object is to provide a monitor of physiological variables with a supporting surface which automatically maintains proper contact between the sensor and the anatomical site being monitored.

Still another object is to provide a monitor of physiological variables which is portable by virtue of low weight, battery power, and low power consumption.

Yet another object is to provide a monitor of physiological variables which is suitable for consumer use by virtue of low cost, simple operation, and simple output format.

One more object is to provide a monitor which is highly suited to thermography.

Still another object is to provide a reliable easy-to-use apparatus to monitor sympathetic nervous system activity.

It is another object of the present invention to provide apparatus for rendering changes of physiological variables as variations of visible or audible output.

Yet another object is to provide apparatus for biofeedback training.

Yet another object is to provide apparatus for biofeedback training that senses a physiological variable which correlates highly with skeleto-muscular and smooth muscular relaxation.

DESCRIPTION OF THE DRAWINGS

These and other objects and advantages of the present invention will hereafter appear in connection with the accompanying drawing wherein.

DESCRIPTION OF THE PREFERRED EMBODIMENTS

Figure 1:
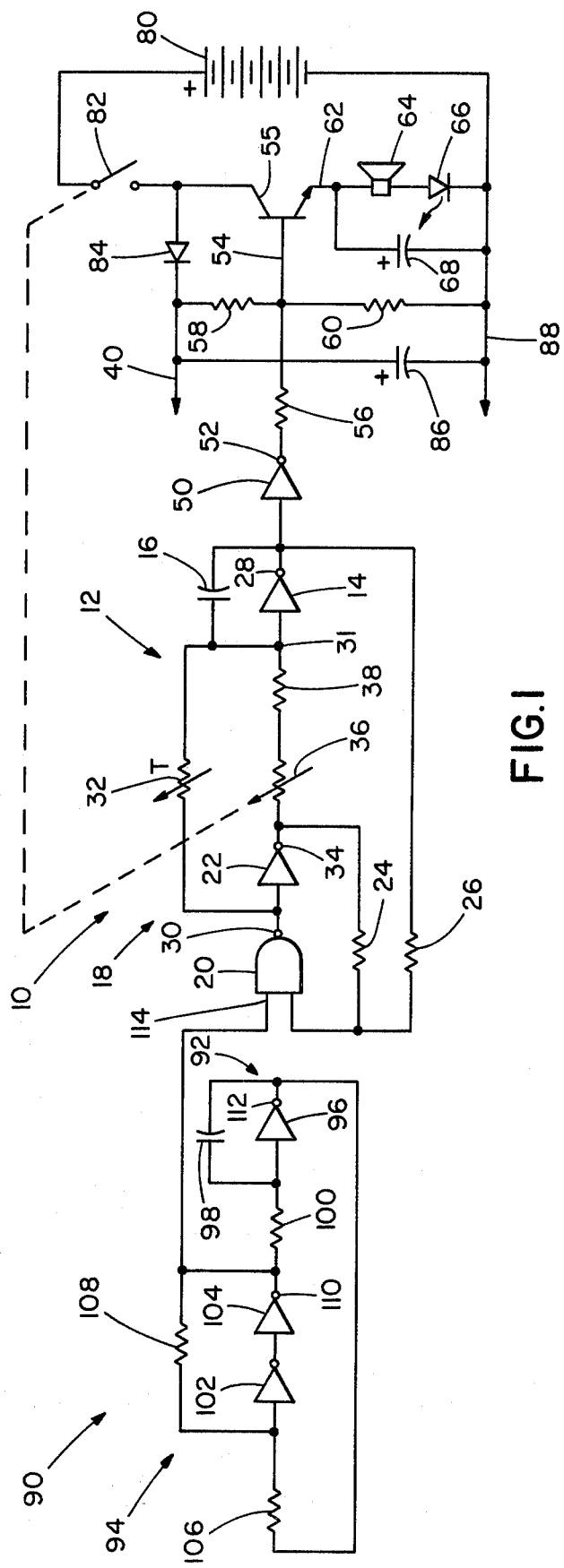
FIG. 1 is an electrical schematic drawing of a preferred embodiment of the present invention.

Referring to FIG. 1, tone circuit 10 comprises integrator 12 and Schmitt type trigger 18. Integrator 12 comprises inverting amplifier 14 which has an internal input offset voltage bias of approximately one-half the supply voltage and integrating capacitor 16. Integrator output 28 has a range from zero volts to the supply voltage. Schmitt trigger 18 comprises nand-gate 20, inverter 22, and resistors 24 and 26. Nand-gate 20 has a nominal switching voltage of one-half the supply voltage. Resistors 24 and 26 create hysteresis thereby producing a lower switching voltage of nominally one-quarter supply voltage and an upper switching voltage of nominally three-quarters supply voltage. Integrator output 28 connects to Schmitt input resistor 26 triggering Schmitt trigger 18 whenever the voltage at 28 exceeds the upper Schmitt switching voltage or is below the lower Schmitt switching voltage. Schmitt output 30 connects to the integrator input 31 through sensor 32. Schmitt output 34 connects to the integrator input 31 through control 36, a variable resistor, in series with fixed resistor 38. Outputs 30 and 34 switch from zero volts to the supply voltage, in opposite directions from each other, whenever the Schmitt switches. Therefore, the nominal absolute value of the input current into integrator input 31 is one-half of the supply voltage 40 multiplied by the difference of the reciprocal of the sum of the resistances of resistors 36 and 38 and of the reciprocal of the resistance of sensor 32. The integrator output has a voltage versus time slope which is proportional to this integrator input current. This slope will cause the integrator output voltage to exceed the Schmitt switching voltage, thus switching the Schmitt, which reverses the direction of the integrator input current and the direction of the output slope. However, variable resistor 36 must be adjusted so that the current through 36 exceeds the current through sensor 32. The voltage waveform at 28 will be generally triangularly shaped and the frequency of repetition will be proportional to the integrator input current, and therefore will decrease as the resistance of the sensor decreases. When the two currents become equal, the tone ceases.

Buffer amplifier 50 amplifies the voltage waveform at 28 in a generally non-linear fashion. Buffer output 52 drives the base 54 of transistor 55 through resistor 56. Resistors 58, 60, and 56 establish both the bias voltage level and the tone voltage level at base 54. Emitter 62 drives the series combination of loudspeaker 64 and light emitting diode 66. Loudspeaker 64 produces audible output, a tone of variable pitch and amplitude, and light emitting diode 66 produces visible output, light of variable intensity, either flashing or steady. Capacitor 68, in conjunction with the characteristics of loudspeaker 64, establishes both a desirable timbre and a decreasing amplitude characteristic with decreasing tone pitch. Since the loudspeaker 64 and light emitting diode 66 are in series, they share the same current. The light output is controlled by the voltage bias at base 54, capacitor 68 and speaker 66.

Power is supplied by battery 80 through on-off switch 82, which is mechanically coupled to tone control 36 so as to operate at one extreme of rotation, to the collector of transistor 55 and through diode 84 to all amplifier, gate, and inverter circuits. Diode 84 protects the circuit from damage due to a reversed battery potential. Capacitor 86 is a power supply filter. Common connection 88 goes to the negative supply connections of all amplifier, gate, and inverter circuits.

Interupter circuit 90, comprising integrator 92 and Schmitt trigger 94, closely parallels tone circuit 10 in structure and operation, but whereas 10 has a repetition rate in the audible range, 90 has a repetition rate of approximately one pulse per second. Integrator 92 comprises amplifier 96, capacitor 98, and input resistor 100. Schmitt trigger 94 comprises invertors 102 and 104, input resistor 106, and feedback resistor 108. The voltage at 110 is integrated by 92 until the voltage at 112 exceeds the switching threshold of Schmitt trigger 94. This switches the Schmitt trigger causing the Schmitt output voltage at 110 to change from zero volts to the supply voltage or vice versa, thus causing integrator 92 to integrate in the opposite direction until the Schmitt switching voltage in this opposite direction is exceeded. Output 110 reverses again, back to its original state, the direction of integration reverses again to its original state, and a new repetition cycle begins. The result is a voltage square wave at output 110, which connects to input 114 of nand-gate 20, thus periodically interupting the operation of tone circuit 10. During the periods of interruption, the tone ceases and the light dims but does not extinguish. Since the light from the light emitting diode never extinguishes it also serves as an on-off pilot light.

Low power consumption, battery compatibility, and low cost are augmented through the use of CMOS integrated circuts manufactured by National Semiconductor of Santa Clara, Calif. The nand-gate is type MM74COO. Amplifiers 14 and 96 and invertors 22, 50, 102, and 104 are all type MM74CO4. Loudspeaker 64 has a 2.25 inch diameter, 45 ohm voice coil impedance, and is rated at 200 milliwatts. It should have a falling low frequency response with a corner at approximately 100 hertz. Light emitting diode 66 can be Texas Instruments of Dallas, Texas type TIL209 or equivalent. Sensor 32 is Fenwal Electronics, Inc. of Framingham, Massachusetts type JA35J1, and has a nominal resistance of 5000 ohms at twenty-five degrees Celsius.

The values or types of other components are as follows:

| | |
|---|---|
| Transistor 55 | 2N3567 |
| Battery 80 | N.E.D.A. 1604 |
| Diode 84 | 1N914 |
| Resistor 24 | 22 kilohms |
| Resistor 26 | 10 kilohms |
| Resistor 38 | 1.5 kilohms |
| Resistor 56 | 2.2 kilohms |
| Resistor 58 | 4.7 kilohms |
| Resistor 60 | 100 kilohms |
| Resistor 100 | 4.7 megohms |
| Resistor 106 | 10 kilohms |
| Resistor 108 | 22 kilohms |
| Variable resistor 36 | 0–5 kilohms, with switch |
| Capacitor 16 | 0.1 microfarad, 100 volt, polyester |
| Capacitor 68 | 10 microfarad, 25 volt, electrolytic |
| Capacitor 86 | 10 microfarad, 25 volt, electrolytic |
| Capacitor 98 | 0.1 microfarad, 100 volt polyester |

All voltages referred to herein are with respect to common connection 88.

Figure 2:
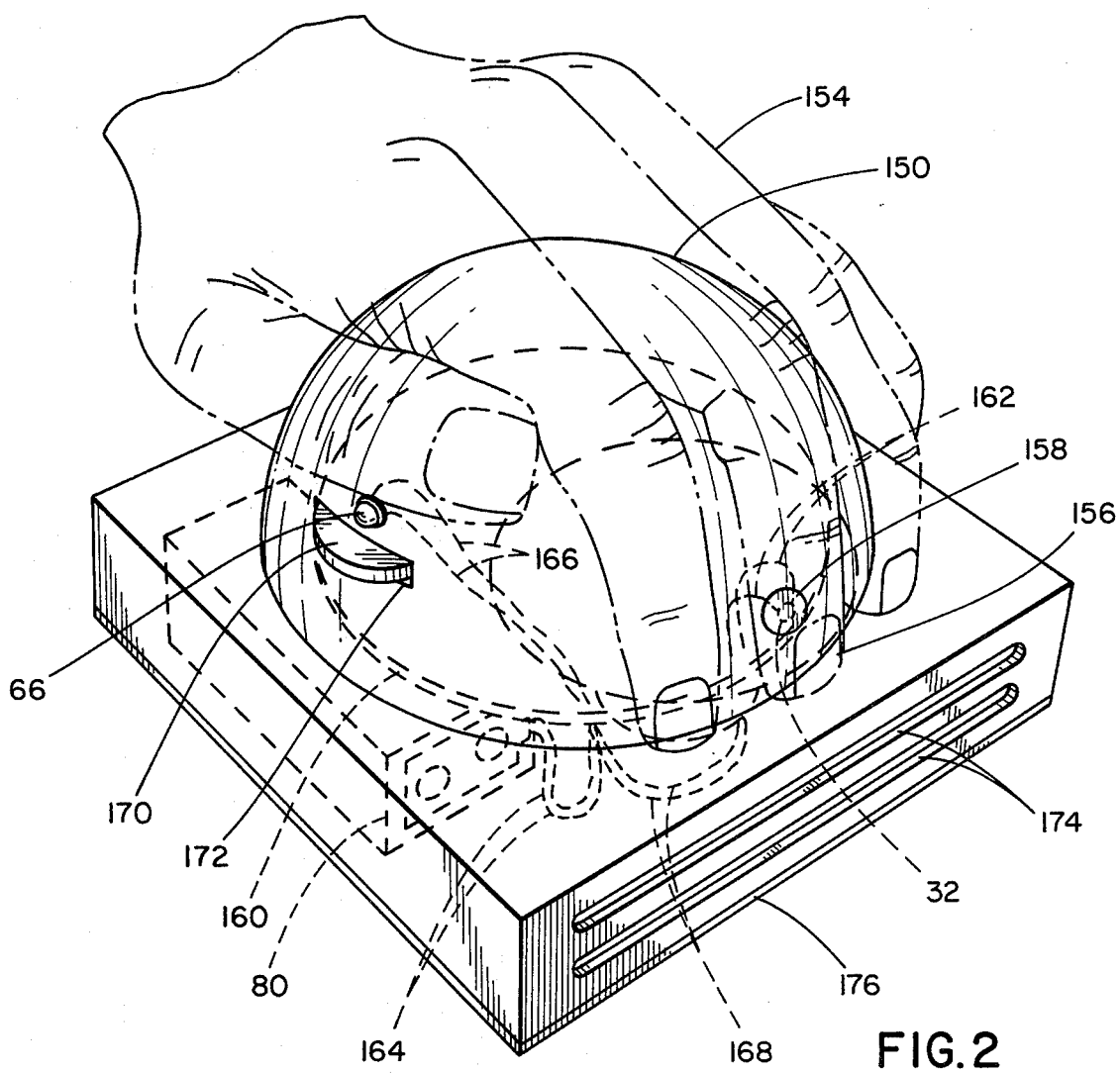
FIG. 2 is a mechanical assembly drawing of a preferred embodiment of the present invention.

Referring to FIG. 2, a hollow hemispherical dome 150, of 0.08 inch thick ABS plastic, rests on a hollow base 152 of wood or plastic, and supports a human hand 154 such that finger 156 rests on disc 158 covering sensor 32. Printed circuit board 160, supported by base 152, carries all components of FIG. 1 except sensor 32, battery 80, light emitting diode 66, and loudspeaker 64, all of which are connected to 160 by wire lead pairs 162, 164, 166, and 168 respectively. Variable resistor (tone control) 36 is operated by rotating dial 170 which extends through slot 172 in dome 150. Loudspeaker 64 is fastened to base 152 which acts as a baffle and acoustic load and sound exits at slots 174. Battery 80 resides in hollow base 152 and is retained by removable bottom 176. Light emitting diode 66 and sensor 32 are mounted on dome 150. Dome serves as both supporting surface and enclosing structure for a portion of apparatus.

Figure 3:
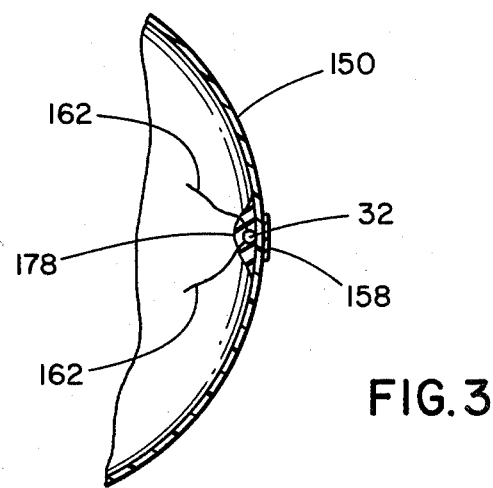
FIG. 3 is a detail drawing of the sensor mounting.

FIG. 3 shows the mounting details of sensor 32 on dome 150 in cross-section. Disc 158 of 0.005 inch thick aluminum five-sixteenths inch in diameter, is fastened to the outside of dome 150 with adhesive. Sensor 32, with wire leads 162 extending inward, is fastened to disc 158 and dome 150 with thermally conductive but electrically non-conductive cement 178, made by mixing two-part filled epoxy cement. Disc and cement conduct heat from site being monitored to sensor.

ALTERNATE EMBODIMENTS

Sensor 32 can be any component or group of components which can be made to have a variable resistance or voltage in response to some physiological variable. Variables suitable for monitoring include, but are not limited to: pressure, stress, light transmission, light reflection, vibration, sound, and temperature.

Base 152 can be another hollow hemispherical dome which mates with 150 to form a hollow sphere. Either 150 or 152 or both may be generally ovoidal.

Dome 150 can be molded to fit and cradle a finger or some other portion of the body.

A second sensor, similar to sensor 32, can be used in place of variable resistor 36 and resistor 38 to allow comparison monitoring.

Earphones can be used in place of, or together with, loudspeaker 64. Visible output can be in the form of a digital display, numeric, bar graph, or otherwise.

USE AS A BIOFEEDBACK SELF-TRAINING DEVICE FOR RELAXATION

The following instructions explain the use of the present invention for biofeedback relaxation training:

1. Place hand over dome with one finger in contact with disc covering sensor. Wait one minute for temperature to stabilize.
2. Rotate control to turn power on and to set tone to a moderately low pitch.
3. Relax by any method desired, such as relaxing one muscle group at a time, controlled slow breathing, Transcendental Meditation, etc.
4. As relaxation is successful, pitch will fall. Select methods which achieve largest drop in pitch.

Those skilled in the art will recognize that these embodiments can be altered and modified without departing from the true spirit of the invention as defined in the accompanying claims.

We claim:

1. Apparatus for monitoring physiological variables said apparatus comprising:
    sensor means for sensing the value of at least one physiological variable,
    said sensor means having at least one property which varies in value in response to the value of said physiological variable,
    output means for generating audible outputs,
    tone means for driving said output means such that said audible output is responsive to variations in the value of said at least one property of said sensor means,
    said tone means comprising Schmitt trigger means and integrator means,
    supporting surface means for establishing contacting relationship between said sensor means and the anatomical site to be monitored,
    said Schmitt trigger means having input and first and second outputs,
    said outputs being complementary,
    said integrator means having an integrator input and an integrator output,
    the first Schmitt trigger output being connected to said integrator input through said sensor means,
    the second Schmitt trigger output being connected through a variable resistor means to said integrator input,
    means for connecting said integrator output to said Schmitt trigger input, and
    means to provide electrical power to the tone means.

2. The apparatus of claim 1 wherein said variable resistor means comprises a series connection of a potentiometer and an integrator resistor, and said means for providing electrical power comprising switch means coupled to the wiper of said potentiometer for connecting the elctrical power to said tone means.

3. A system for self-monitoring by a subject of physiological variables by measuring the temperature of the subject's hand, said system including a base, sensor means for sensing the temperature of at least some portion of the subject's hand, said sensor means having conductor means integral thereto, surface means on said base for mounting said sensor means thereon with said conductor means totally within the space defined by said surface means and said base, said sensor means positioned to abut the portion the subject's hand, when the subject's hand rests on the surface means, sensor output means in said base for providing a signal varying the response to variations in the temperature of said portion of the subject's hand, system output means in said base for generating output signal detectable by at least one of the human senses, and said system output means operating responsive to said sensor output signal to provide an output detectable by said subject, whereby variations in the temperature of the said portion of the subject's hand is detected by the subject without the necessity of attaching cord connected electrodes to the subject.

4. The system of claim 3 wherein said surface means is dome shaped and thereby contoured to fit a cupped human hand.

5. The system of claim 3 wherein said system output means comprises audio transmitter means, tone circuit means for generating an output frequency for driving said audio transmitter means, and means for varying the output frequency of said tone circuit means responsive to variations in the output signal of said sensor means, whereby the audio output of said audio transmitter means varies in response to the hand temperature being monitored.

6. The system of claim 5 where said system output means comprises:

means for energizing light emitting means with intensity varying responsive to the output of said tone circuit means.

7. The system of claim 3 wherein said system output means comprise, tone circuit means for producing output frequencies, a series circuits comprising a loud speaker and a light emitting drode, and means for driving both the loud speaker and the light emitting drode using the same series current responsive to the output frequencies of said tone circuit means.

8. The system of claim 7 wherein said tone circuit means comprises Schmitt trigger means and integrator means, coupling means for coupling the output of said Schmitt trigger means to said integrator means, said coupling means including said sensor means operating to vary the output frequency of said tone circuit means responsive to variations in said sensor output signal caused by variations in the monitored temperature, and means for coupling the output of the integrator means to the input of the Schmitt trigger means.

9. The system of claim 8 wherein said Schmitt trigger means comprises a two input NAND gate having an output connected to an inverter, means for coupling the output of the inverter to one input of said two input NAND gate through a first resistor means, means for coupling the output of the integrator to the one input of the two input NAND gate through a second resistor means, said coupling means including means for coupling the output of said NAND gate through said sensor means to the input of said integrator means, integrator resistor means for also coupling the output of said inverter means to the input of said integrator means, said sensor means comprising thermistor means, said integrator resistor means including variable resistor means for selectively controlling the amplitude and frequency of the output of said tone circuit, and means for coupling interrupt circuit means to the other input of said NAND gate means, whereby the tone from the tone circuit is periodically interrupted.

10. A system for self-monitoring by a subject of physiological variables by measuring the temperature of the subject's hand, said system including a base, sensor means for sensing the temperature of at least a portion of the subject's hand, surface means on said base for mounting said sensor means thereon positioned to abut the portion of the subject's hand, when the subject's hand rests on the surface means, sensor output means providing a signal varying in response to variations in the temperature of said portion of the subject's hand, system output means for generating an output signal detectable by at least one of the human senses, said system output operating responsive to said sensor output signal to provide an output detectable by said subject, whereby variations in the temperature of the said portion of the subject's hand is detected by the subject without the necessity of attaching electrodes to the subject, said system output means comprising tone circuit means for producing output frequencies, a series circuit comprising a loud speaker and a light emitting diode, means for driving both the loud speaker and the light emitting diode using the same series current responsive to the output frequencies, of said tone circuit means, said tone circuit means comprising Schmitt tirgger means an integrator means, coupling means for coupling the output of said Schmitt trigger means to said integrator means, said coupling means including said sensor means operating to vary the output frequencies of said tone circuit means responsive to variations in the monitored temperature, means for coupling the output of the integrator means to the input of the Schmitt trigger means, said base comprising acoustic baffle means, and filter capacitor means bridging said system output means for assuring production of a pleasing output tone.

* * * * *

UNITED STATES PATENT AND TRADEMARK OFFICE
CERTIFICATE OF CORRECTION

PATENT NO. : 4,246,906
DATED : January 27, 1981
INVENTOR(S) : Jack S. Winberg and Richard A. Karlin It is certified that error appears in the above-identified patent and that said Letters Patent are hereby corrected as shown below:

| | |
|---|---|
| Column 2, Line 11 | Delete "ski" and insert instead --skin--. |
| Column 2, Line 51 | Delete "snesor" and insert instead --sensor--. |
| Column 5, Line 5 | Delete "circuts" and insert instead --circuits--. |
| Column 5, Line 56 | After "aluminum" insert --,--. |

Signed and Sealed this

Fifth Day of May 1981

[SEAL]

Attest:

RENE D. TEGTMEYER

Attesting Officer     Acting Commissioner of Patents and Trademarks